(12) United States Patent
Paulsen et al.

(10) Patent No.: US 12,357,648 B2
(45) Date of Patent: *Jul. 15, 2025

(54) INJECTABLE ANTIBIOTIC FORMULATIONS AND USE THEREOF

(71) Applicant: Dechra Veterinary Products, LLC, Overland Park, KS (US)

(72) Inventors: Neil E. Paulsen, Overland Park, KS (US); Gail L. Dempsey, Overland Park, KS (US); Michael S. Daniel, Overland Park, KS (US); Tiffany G. Tomlinson, Overland Park, KS (US); Douglas I. Hepler, Overland Park, KS (US); Raymond Petzold, Overland Park, KS (US)

(73) Assignee: Dechra Veterinary Products, LLC, Overland Park, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/652,718

(22) Filed: May 1, 2024

(65) Prior Publication Data

US 2024/0285662 A1 Aug. 29, 2024

Related U.S. Application Data

(63) Continuation of application No. 18/123,811, filed on Mar. 20, 2023, now Pat. No. 12,005,071, which is a continuation of application No. 17/197,838, filed on Mar. 10, 2021, now Pat. No. 11,628,180, which is a continuation of application No. 16/937,094, filed on Jul. 23, 2020, now abandoned, which is a continuation of application No. 16/359,197, filed on Mar. 20, 2019, now Pat. No. 10,729,709, which is a continuation of application No. 15/179,625, filed on Jun. 10, 2016, now Pat. No. 10,286,003.

(60) Provisional application No. 62/312,382, filed on Mar. 23, 2016, provisional application No. 62/307,284, filed on Mar. 11, 2016, provisional application No. 62/173,850, filed on Jun. 10, 2015.

(51) Int. Cl.
| | | |
|---|---|---|
| *A61K 31/7052* | (2006.01) | |
| *A61K 9/00* | (2006.01) | |
| *A61K 45/06* | (2006.01) | |
| *A61K 47/14* | (2017.01) | |
| *A61K 47/44* | (2017.01) | |

(52) U.S. Cl.
CPC ........ *A61K 31/7052* (2013.01); *A61K 9/0019* (2013.01); *A61K 45/06* (2013.01); *A61K 47/14* (2013.01); *A61K 47/44* (2013.01)

(58) Field of Classification Search
CPC .. A61K 31/7052; A61K 9/0019; A61K 45/06; A61K 47/44

USPC ............................................................ 514/29
See application file for complete search history.

(56) References Cited

U.S. PATENT DOCUMENTS

| | | | |
|---|---|---|---|
| 6,984,403 B2 | 1/2006 | Hagen et al. | |
| 7,108,865 B2 | 9/2006 | Curatolo et al. | |
| 7,919,522 B2 | 4/2011 | Soll et al. | |
| 8,710,019 B2 * | 4/2014 | Huber | A61K 31/7052 514/29 |
| 10,286,003 B2 * | 5/2019 | Paulsen | A61K 45/06 |
| 10,729,709 B2 * | 8/2020 | Paulsen | A61K 31/7052 |
| 11,628,180 B2 * | 4/2023 | Paulsen | A61K 31/7052 514/29 |
| 12,005,071 B2 * | 6/2024 | Paulsen | A61K 31/7052 |
| 2002/0044965 A1 * | 4/2002 | Curatolo | A61P 31/04 514/28 |
| 2007/0293446 A1 | 12/2007 | Soll et al. | |
| 2008/0160067 A1 | 7/2008 | Boeckh et al. | |

FOREIGN PATENT DOCUMENTS

| | | |
|---|---|---|
| WO | WO 1999/27906 A1 | 6/1999 |
| WO | WO 2000/059475 A1 | 10/2000 |
| WO | WO 2002/07736 A1 | 1/2002 |
| WO | WO 2005/044254 A1 | 5/2005 |
| WO | WO 2006/052098 A1 | 5/2006 |
| WO | WO 2007/024719 A2 | 3/2007 |
| WO | WO 2009/013331 A1 | 1/2009 |

OTHER PUBLICATIONS

BASF Technical Information, "Kolliphor™ HS 15 Macrogol 15 Hydroxystearate Ph. Eur. Polyoxyl 15 Hydroxystearate USP," Mar. 2, 2012, pp. 1-2.
Extended European Search Report and Search Opinion received for EP Patent Application No. 168083396.2, mailed Dec. 12, 2018, 7 pages.
International Preliminary Report on Patentability received for PCT Application No. PCT/US2016/036936, mailed Dec. 21, 2017, 7 pages.
International Search Report and Written Opinion received for PCT Application No. PCT/US2016/036936, mailed Sep. 7, 2016, 7 pages.
Ku et al., "Solutol HS15 as a Novel Excipient," PharmTech, vol. 34, No. 11, Nov. 2, 2010, pp. 1-4.
Notice of Reasons for Rejection received for JP Patent Application No. 2018-516392, mailed Feb. 26, 2020, 12 pages (6 pages of English Translation and 6 pages of Original Document).

* cited by examiner

*Primary Examiner* — Ganapathy Krishnan
(74) *Attorney, Agent, or Firm* — DLA Piper LLP (US)

(57) ABSTRACT

Provided herein are pharmaceutically acceptable compositions containing macrolide antibiotics, in particular azithromycin. In particular, compositions containing azithromycin with low toxicity, especially for administration to felines, are provided herein.

17 Claims, No Drawings

INJECTABLE ANTIBIOTIC FORMULATIONS AND USE THEREOF

CROSS REFERENCE TO RELATED APPLICATIONS

This application is a continuation application of U.S. application Ser. No. 18/123,811 filed Mar. 20, 2023; which is a continuation application of U.S. application Ser. No. 17/197,838 filed Mar. 10, 2021, now issued as U.S. Pat. No. 11,628,180; which is a continuation application of U.S. application Ser. No. 16/937,094 filed Jul. 23, 2020; which is a continuation application of U.S. application Ser. No. 16/359,197 filed Mar. 20, 2019, now issued as U.S. Pat. No. 10,729,709; which is a continuation application of U.S. application Ser. No. 15/179,625 filed Jun. 10, 2016, now issued as U.S. Pat. No. 10,286,003; which claims the benefit under 35 USC § 119(e) to U.S. Application Ser. No. 62/312,382 filed Mar. 23, 2016; U.S. Application Ser. No. 62/307,284 filed Mar. 11, 2016 and U.S. Application Ser. No. 62/173,850 filed Jun. 10, 2015. The disclosure of each of the prior applications is considered part of and is incorporated by reference in the disclosure of the application.

BACKGROUND OF THE INVENTION

Field of the Invention

The invention relates generally to injectable antibiotic formulations and more specifically to a formulation of an antibiotic macrolide compound with low toxicity.

Background Information

The present invention is based on the seminal discovery of compositions containing an antibiotic macrolide active compound, especially azithromycin, formulated for injection to small subjects (about 100 pounds or less), such as felines. The formulations of the invention allow for effective treatment of infections with surprisingly lower toxicity than other available macrolide formulations.

Azithromycin, for example, is used by veterinarians to treat a range of bacterial infections in veterinary subjects such as dogs and cats, including streptococci, staphylococci, *Bartonella henselae*, some species of *Chlamydia*, *haemophilus* spp, *mycoplasma* spp, *Borrelia burgdorferi* and others. The mechanism of action of azithromycin is binding to the P site of the 50S ribosomal subunit of those microorganisms that are susceptible to it, thereby interrupting the microorganism's RNA-dependent protein synthesis. It is a semi-synthetic macrolide antibiotic derived from erythromycin. Azithromycin is a more popular choice than erythromycin in the treatment of dogs and cats because it has a longer half-life and is better absorbed by both species.

However, there are common potential side effects associated with macrolides such as azithromycin, including gastrointestinal problems like abdominal discomfort, vomiting and diarrhea. Angioedema and jaundice can also result from taking these drugs. More serious potential side effects can include cardiac arrhythmia, ventricular tachycardia and issues with renal and hepatic function.

The drug is particularly problematic for use in cats. Azithromycin in particular is cleared very slowly from feline tissue, resulting in dosage schedules that are very convenient, but an increased risk of toxicity and adverse effects in cats. Given the broad utility of azithromycin for the treatment of various infections, a need therefore exists for compositions containing azithromycin that are at least as potent and effective but have lower toxicity, especially in felines.

SUMMARY OF THE INVENTION

Provided herein is a composition, comprising:
(i) a hydrated form of a macrolide, such as a mectin or mycin, preferably a mono- or di-hydrated macrolide, such as an azilide and most especially azithromycin;
(ii) a suitable solvent; and
(iii) an excipient.

In certain aspects, the solvent is triacetin. In certain embodiments, the solvent is present in an amount of about 38.0% w/w. In one aspect, the solvent is caprylic/capric triglycerides or caprylic triglycerides. In other embodiments, the triglyceride solvent is present in an amount of about 54.0% w/w. In some aspects, the composition further comprises castor oil, such as KOLLIPHOR™ (Polyoxyl 15 Hydroxystearate) or RH 40™. In certain aspects, the macrolide is present in an amount of about 7.0% w/w. In other aspects, the composition is formulated for administration by injection.

Also provided herein is a method of treating an infection in an animal or a small human subject, generally about 100 pounds or less in weight with a single injection of a composition of the invention, requiring only one dose in a single injection for resolution of the infection up to 100%. No additional dosing for the infection treated should be required (although, of course, re-dosing is possible if a separate infection occurs).

The animal may be a feline including, but not limited to, a domestic cat. The method provided herein includes administering an effective amount of a composition comprising (i) a macrolide such as azithromycin, preferably in a di- or mono-hydrate form; (ii) a suitable solvent; and (iii) an excipient. In some aspects, the method further comprises an additional antibiotic that is co-administered with the compositions provided herein. In other aspects, the compositions are administered by injection to the feline for the treatment of an infection.

DETAILED DESCRIPTION OF THE INVENTION

The following terms, definitions and abbreviations apply. Abbreviations used herein have their conventional meaning within the chemical and biological arts.

The term "patient" refers to organisms to be treated by the methods of the disclosure. Such organisms include, but are not limited to, felines such as domestic cats. In the context of the disclosure, the term "subject" generally refers to an individual who will receive or who has received treatment described below (e.g., administration of the compounds of the disclosure, and optionally one or more additional therapeutic agents).

The term "therapeutically effective amount" means the amount of the compound or pharmaceutical composition that will elicit the biological or medical response of a patient or tissue that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The disclosure also provides pharmaceutical compositions comprising at least one active compound in an amount effective for treating a disorder, and a pharmaceutically acceptable vehicle or diluent. The active compound will be a macrolide antibiotic, including the mectins (including, without limitation, doximectin and abimectin) and the mycins (including, without limitation, roxithromycin, clarithromycin, tulathromycin, gamithromycin, dirithromycin, fidaxomicin, megalomicin, erythromycin and the like), potentially an azilide, and most preferably azithromycin. The active agents are most preferably hydrated; e.g., a monohydrate or dehydrate form of the molecule. The compositions of the disclosure may contain other therapeutic agents than azithromycin and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the disclosure may also be formulated into therapeutic compositions as natural or salt forms. Pharmaceutically acceptable non-toxic salts include the base addition salts (formed with free carboxyl or other anionic groups), which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like.

Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure, with hydrates being particularly preferred. It should be noted that while the hydrate molecules will contribute water to the pharmaceutical composition, it is most preferred that no other water source be included.

The disclosed pharmaceutical compositions could be administered by any suitable means, for example, orally, sublingually; buccally; parenterally, such as by subcutaneous, intravenous, intramuscular, intrathecal, or intracisternal injection or infusion techniques (e.g., as sterile injectable non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. Preferably, however, the administration will be by injection or infusion; e.g., by intravenous, subcutaneous or intramuscular routes of administration.

The pharmaceutical compositions for the administration of the compounds of this embodiment either alone or in combination with other agents, e.g., anti-inflammatories, analgesics, other antibiotics, anti-fungals, anti-virals and other pharmaceutically active components, although the composition is effective against infection with a hydrated macrolide, preferably an azilide, most preferably azrithromycin as the sole active agent present.

The composition may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a carrier suitable for use in an injection. In the pharmaceutical composition the active object compound is included in an amount sufficient to produce the desired effect upon the process or condition of diseases.

The pharmaceutical compositions is preferably in the form of a sterile injectable oleaginous solution or suspension. The composition may be formulated according to the known art using those suitable dispersing or wetting agents and suspending agents which have been mentioned above, preferably not including water. The solvent used in the suspension is preferably one which is miscible with a medium chain triglyceride surfactant, preferably a C8 trigylceride.

In certain aspects, the solvent is triacetin (glyceryl triacetate or glycerol triacetate). In certain such embodiments, the solvent is present in an amount of about 23 to 70%, 30 to 60%, 40 to 55%, 34 to 45%, and preferably about 38.0% w/w. In another aspect, the solvent is caprylic/capric (C10 and/or C8) triglycerides or caprylic (C8) triglycerides, most preferably a C8 triglyceride. In such embodiments, the triglyceride solvent is present in an amount of about 20 to 60%, 40 to 55% and preferably about 54.0% w/w. Other suitable solvents may be benzyl alcohol, 2-ethoxy (2-ethoxy) ethanol, ethyl oleate, ethyl acetate, ethanol, ethyl benzoate, benzyl benzoate, 2-pyrrolidone, DMSO and 2-methyl-2pyrrolidone and 2-pyrrolidone.

The composition most preferably includes at least a solvent and a surfactant; most preferably, triacetin and a C8 triglyceride. In some aspects, the composition comprises a surfactant such as castor oil or hydrogenated castor oil, such as KOLLIPHOR™ HS15 (Polyoxyl 15 Hydroxystearate) or RH 40 or TPGS, polysorbate (e.g., 20 and 80) or lecithen. No depot is formed in the composition of the invention.

The formulation can also contain other inert ingredients such as antioxidants or preservatives. Antioxidants such as a propyl gallate, BHA (butylated hydroxy anisole), BHT (butylated hydroxy toluene) monothioglycerol, tri-ethyl citrate, citric acid, TBHQ (tert-butyl hydroquinone) and the like may be added to the present formulation. The antioxidants are generally added to the formulation in amounts of from about 0.01 to about 2.0% (w/v). Preservatives such as the parabens (methylparaben and/or propylparaben) are suitably used in the formulation in amounts ranging from about 0.01 to about 2.0 w/v.

The formulation of the present invention may be prepared by adding a dispersion of hydrogenated castor oil in acetylated monoglycerides, propyl dicaprylates/dicaprates or caprylic/capric triglycerides to a solution comprising the therapeutic agent. Since the formulation is intended for injection, it is desirable that it be sterilized. Surprisingly, heat sterilization may be used in crafting the formulations of the invention without adversely affecting the stability or potency of the macrolide therapeutic agent.

In the methods described herein, an appropriate dosage level will generally be about 0.01 to about 50 mg/kg, such as, for example, 0.25 to about 15 mg/kg per day, such as 2.5 to about 14 mg/kg per day. Within this range the dosage may be 0.25 to 0.5, 0.25 to 14 mg/kg, 7 to 10 mg/kg (including all intermediate dosages, such as 7.1, 7.2, 7.3 etc. mg/kg) and preferably about 7 mg/kg, all in a single injection form. In this form, the compounds need only be administered by single injection, one time for an entire course of treatment to clinically resolve an infection up to 100% elimination.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

Example I

Efficacy and Safety

This study evaluated the effectiveness and field safety of a single injection of a triglyceride azithromycin formulation for the treatment of skin and soft tissue infections (abscesses) in cats.

Twenty-two (22) cats were enrolled in the study at 2 study sites. All 22 cats were treated with the investigational veterinary product (IVP), and 20 were included in the efficacy evaluation.

Cats enrolled in the study presented to the clinic with skin and soft tissue infections. On Day 0, a physical examination was conducted, which included assignment of a wound clinical score based on swelling, pain, and exudate. For inclusion in the study, the wound clinical score had to be a minimum of 5, with a minimum exudate score of 2. A swab was obtained from the wound (following lancing for closed abscesses) and shipped to each investigator's preferred contract laboratory for bacterial culture. Wound management procedures were allowed after swab collections, but the only permissible cleaning agents were saline or tap water. Blood and serum samples were collected, and hematology and serum chemistry analyses were conducted in-clinic.

The cats were dosed via subcutaneous injection with about 7 mg/kg of a composition consisting of 7% azithromycin DH (dihydrate), 54% caprylic (C8) triglycerides, 38% triacetin and 1% KOLLIPHOR™ HS-15 (Polyoxyl 15 Hydroxystearate), at which time observations were made for injection pain:

Dosing Chart

| Weight (kg) | Weight (lbs) | Injection Volume (mL) | Dose Rate (mg/kg) |
|---|---|---|---|
| 1.5 & 2.0 | >3.3 & .5 4.4 | 0.2 | 7.0-9.3 |
| >2.0 & 5_3.0 | >4.4 & 6.6 | 0.3 | 7.0-10.0 |
| >3.0 & 5. 4.0 | >6.6 & 8.8 | 0.4 | 7.0-9.0 |

Dosing Chart

| Weight (kg) | Weight (lbs) | Injection Volume (mL) | Dose Rate (mg/kg) |
|---|---|---|---|
| >4.0 & 5.0 | >8.8 & 11.0 | 0.5 | 7.0-8.5 |
| >5.0 & 5_6.0 | >11.0 & 13.2 | 0.6 | 7.0-8.2 |
| >6.0 & 5. 7.0 | >13.2 &.5 15.4 | 0.7 | 7.0-8.0 |
| >7.0 & 8.0 | >15.4 & 5 17.6 | 0.8 | 7.0-7.9 |
| >8.0 &5 9.0 | >17.6 & 5 19.8 | 0.9 | 7.0-7.8 |
| >9.0 & 5 10.0 | >19.8 & 22.0 | 1.0 | 7.0-7.7 |

Observations were made hourly for the first 4 hours postinjection, and an injection site observation and temperature were obtained at 4 hours post-injection. At approximately 24 hours post-injection, another temperature and injection site evaluation were conducted.

At the interim study visit on Day 7 (±2), a wound clinical score was assigned and the injection site was examined for any abnormalities. At the final visit on Day 14 (±2), a physical examination was conducted, a wound clinical score was assigned, and the injection site was evaluated for any abnormalities. In addition, blood and serum samples were collected for a final hematology and serum chemistry analysis.

A successful case was defined as a cat with a concluding wound score of 1 for at least two of the three variables, and an improvement of at least 1 or a score of 1 in the third variable. Since all cases were successful, there were no Day 14 swab samples obtained for culture.

Based on wound clinical scores, 20 of 20 cats in the effectiveness analysis were considered successful cases, resulting in an efficacy of 100%.

| Case ID | D0 Score | D7 Score | D14 Score | Day 0 Culture | Day 14 Culture |
|---|---|---|---|---|---|
| ROB01 | 7 | 4 | 3 | Pasteurella species, Enterobacter cloacae, Citrobacter freundii, & Pseudomonas species | NA |
| ROB02 | 8 | 3 | 3 | Pasteurella species | NA |
| ROB03 | 7 | 3 | 3 | Pasteurella species & non-enteric gram negative rod | NA |
| ROB04 | 7 | 3 | 3 | Pasteurella species & Staphylococcus schleiferi | NA |
| ROB05 | 9 | 3 | 3 | Pasteurella species | NA |
| ROB06 | 9 | 3 | 3 | Pasteurella species | NA |
| ROB07 | 7 | 3 | 3 | Hemolytic Staphylococcus species & Serratia fonticola | NA |
| ROB08 | 9 | 3 | 3 | Pasteurella species | NA |
| ROB09 | 7 | 4 | 3 | Pasteurella multocida, alpha-hemolytic Streptococcus sp, & Pasteurella species | NA |
| ROB10 | 7 | 3 | 3 | Pseudomonas putida & Pasteurella species | NA |
| ROB11 | 7 | 3 | 3 | Pasteurella species & non-enteric gram negative rod | NA |
| ROB12 | 9 | 4 | 3 | Pasteurella species & non-enteric gram negative rod | NA |
| SIF01 | 7 | 3 | 3 | Gram positive fusiform anaerobe | NA |
| SIF02 | 6 | 3 | 3 | No pathogens isolated | NA |
| SIF03 | 9 | 3 | 3 | Staphylococcus aureus | NA |
| SIF04 | 9 | 3 | 3 | Coagulase negative Staphylococcus & mixed gram positive and negative anaerobic rods | NA |
| SIF05 | 9 | 3 | 3 | Coagulase negative Staphylococcus sp. | NA |
| SIF06 | 9 | 3 | 3 | Gram negative bacilli | NA |

Example II

Dose Testing

The dose of active described in Example 1 was halved to determine whether efficacy could be achieved at a lower dosing concentration. In particular, this study evaluated the safety and effectiveness of a single administration of an azithromycin injectable formulation (IVP) for the treatment of skin infections (wounds and abscesses) in cats when administered at two dose levels as compared to a negative control of sterile saline (CVP).

Twenty-one (21) cats were enrolled in the study at 2 study sites. Seven (7) cats were treated with the IVP at a dose rate of 7 mg/kg (Group C), 7 cats were treated with the IVP at a dose rate of 3.5 mg/kg (Group B), and 7 cats were treated with the CVP (Control, Group A). All 21 cats were included in the safety evaluation, while 18 were included in the effectiveness evaluation.

Cats enrolled in the study presented to the clinic with skin infections. On Day 0, a physical examination was conducted, which included assignment of a wound clinical score based on swelling, pain, and exudate. For inclusion in the study, the wound clinical score had to be a minimum of 5, with a minimum exudate score of 2. A swab was obtained from the wound (following lancing for closed abscesses) and shipped to each investigator's preferred contract laboratory for bacterial culture. Wound management procedures were allowed after swab collections, but the only permissible cleaning agents were saline or tap water.

The cats were dosed via subcutaneous injection and the injection site was recorded. At the first interim study visit on Day 3 (−1 day), a physical examination was conducted, a clinical score was assigned, and the injection site was examined for abnormalities. If there was no improvement in the clinical score, or if the exudate score was 3 (purulent exudate present), the cat was withdrawn from the study and a swab sample was collected for bacterial culture.

At the second interim study visit on Day 7 (±1 day), a physical examination was conducted, a clinical score was assigned, and the injection was examined for abnormalities. If the case was a treatment failure based on the clinical score (success=concluding clinical score of 1 for at least two of the three variables, and an improvement of at least 1 or a score of 1 in the third variable as compared to Day 0 clinical score), it was withdrawn from the study and a swab sample was collected for bacterial culture.

For cats that were treatment successes on Day 7, a final study visit was conducted on Day 14 (±2 days). A clinical score was assigned and, since there were no cases with recurrence, no final swab samples were collected on Day 14 for bacterial culture.

Based on wound clinical scores, 6 of 6 cats in Group C were considered successful cases; 6 of 7 cats in Group B were considered successful cases; and 2 of 5 cats in Group A were considered successful cases. Thus, the efficacy for the azithromycin 7 mg/kg dose was 100.0% versus an efficacy of 85.7% for the 3.5 mg/kg dose and an efficacy of 40.0% for the control group.

Example III

Toxicity Evaluation

Dose levels of control, 7 mg/kg One (Day 0) and 35 mg/kg One (Day 0) of azithromycin active prepared in the composition of Example I were evaluated for adverse reactions in felines.

Cats were dosed as described in the Examples above via subcutaneous (SQ) injection into the right dorsoscapular area. Injection sites were evaluated once in acclimation, at four hours post-dosing, and once daily from Days 1 to 7. Rectal temperatures were taken at four hours post-dosing, once daily post-dosing, then discontinued at three days post-dosing as rectal temperatures remained within test facility reference ranges. Blood was collected for clinical pathology (hematology and clinical chemistry) from all cats on Study Days −7, 3, and 7. Standard six-lead and rhythm strip electrocardiograma) were obtained from each cat once during acclimation, on Day 0 at two hours post-dosing, on Day 1 at 24 hours post-dosing, and then on Day 7.

Cats remained in good general health throughout the study. All adverse events (AEs) observed during the study were non-serious and self-limiting. AEs related to test article administration were as follows: There were no serious adverse events noted. There were no notations of erythema, heat, or swelling at injection sites. One cat in group T5 was noted to be painful at 4 h post-dosing. The site was non-painful by the next scheduled observation.

Minor abnormalities were noted for serum chemistry and hematology parameters. Elevations noted in creatinine phosphokinase and lactate dehydrogenase were consistent with handling stress during blood collection. Several other clinical chemistry parameters were noted to be outside of test facility reference ranges on multiple cats during the study. None of these abnormalities were of clinical or toxicological concern.

Electrocardiogramere reviewed by the cardiologist and showed no evidence of cardiac pathology. Two cats had minor abnormalities on ECG. One cat from group T1 had multiple ventricular premature contractions; and one cat in group T5 had sinus arrhythmia with frequent escape beats. Both of these were noted on the Day 7 ECG. No cardiovascular abnormalities were noted on physical examination of either cat during acclimation or during the study. Given the lack of other clinical signs of cardiac disease, and the isolated nature of these findings, they have no clinical or toxicological relevance and are therefore unrelated to test article administration.

Rectal temperatures remained within test facility reference ranges throughout the entire study. Dose group had no effect on clinical chemistry, hematology, ECG, rectal temperature, physical examination, body weight, and food consumption outcomes.

In conclusion, azithromycin 7% injection, when administered SQ in cats at 1 and 5 times the proposed label dose versus a placebo control was not associated with any clinically or toxicologically relevant effects on clinical chemistry, hematology, ECG, rectal temperature, or food consumption.

Although the invention has been described with reference to the above description, it will be understood that modifications and variations are encompassed within the spirit and scope of the invention. Accordingly, the invention is limited only by the following claims.

What is claimed is:

1. A pharmaceutical composition, comprising:
   (i) a macrolide;
   (ii) at least two solvents; and
   (iii) an excipient;
wherein a first solvent is triacetin present in an amount of at least 23% w/w,
wherein a second solvent is present in an amount of about 20-60%, and wherein no water, other than water molecules present as hydrates, is included in the composition.

2. The composition of claim 1, wherein the second solvent is selected from the group consisting of a triglyceride, an acetylated monoglyceride, propyldicaprylates/dicaprates and caprylic/capric triglycerides.

3. The composition of claim 1, wherein the macrolide is a mono- or di-hydrate macrolide.

4. The composition of claim 3, wherein the macrolide is azithromycin.

5. The composition of claim 1, wherein the triacetin is present in an amount of about 38% w/w.

6. The composition of claim 1, wherein the excipient comprises a surfactant.

7. The composition of claim 6, wherein the surfactant is selected from the group consisting of castor oil, hydrogenated castor oil, polyoxyl 15 hydroxystearate, polyethylene glycol 40 hydrogenated castor oil, propyl dicaprylate/dicaprate, D-α-tocopherol polyethylene glycol 1000 succinate (TPGS), polysorbate or lecithin.

8. The composition of claim 7, wherein the surfactant is polyoxyl 15 hydroxystearate.

9. The composition of claim 7, wherein the polyoxyl 15 hydroxystearate is present in an amount of about 1% w/w.

10. The composition of claim 2, wherein the triglyceride is a caprylic or caprylic/capric triglyceride.

11. The composition of claim 10, wherein the triglyceride is present in an amount of about 54.0% w/w.

12. The composition of claim 4, wherein the azithromycin is present in an amount of about 7.0% w/w.

13. The composition of claim 1, wherein the composition is formulated for injection.

14. A method of treating an infection in a subject weighing less than about 100 pounds, comprising administering an effective amount of a composition of claim 1.

15. The method of claim 14, further comprising administering an additional antibiotic.

16. The method of claim 14, wherein the subject is a feline.

17. The method of claim 14, wherein the composition is administered by injection.

* * * * *